(12) United States Patent
Barrera et al.

(10) Patent No.: US 8,246,558 B2
(45) Date of Patent: Aug. 21, 2012

(54) QUICK CONNECT APPARATUS AND METHOD

(76) Inventors: Rafael Barrera, Columbus, IN (US); Myron Moorman, Columbus, IN (US)

( * ) Notice: Subject to any disclaimer, the term of this patent is extended or adjusted under 35 U.S.C. 154(b) by 400 days.

(21) Appl. No.: 12/497,637

(22) Filed: Jul. 3, 2009

(65) Prior Publication Data
US 2011/0004134 A1    Jan. 6, 2011

(51) Int. Cl.
*A61F 5/00* (2006.01)
*A61F 2/74* (2006.01)
(52) U.S. Cl. ............... 602/16; 602/12; 602/19; 602/23; 623/27
(58) Field of Classification Search ............... 602/5, 12, 602/16, 23, 25–29; 403/345, 348–350; 623/27, 623/48, 31, 32; 128/882
See application file for complete search history.

(56) References Cited

U.S. PATENT DOCUMENTS

| | | | |
|---|---|---|---|
| 4,549,418 A * | 10/1985 | Hall | ................................. 70/85 |
| 5,242,378 A * | 9/1993 | Baker | ............................. 602/23 |
| 6,129,689 A * | 10/2000 | Dibello | ........................... 602/16 |
| 6,171,535 B1 | 1/2001 | Glynn | |
| 6,736,567 B1 | 5/2004 | Dibello | |
| 7,018,352 B2 | 3/2006 | Pressman et al. | |

* cited by examiner

*Primary Examiner* — Patricia Bianco
*Assistant Examiner* — Kari Petrik
(74) *Attorney, Agent, or Firm* — Roberts IP Law; John Roberts

(57) ABSTRACT

A device and method for releasably connecting together two elements, such as two orthotic devices, or two elements of an orthotic device is provided. A quick connect apparatus and method of use is disclosed that quickly and easily enables a user to attach and detach two devices or two elements of a device, such as the elements of an orthosis or a prosthetic. An example device that may easily be converted back and forth between an ankle-foot orthosis and a knee-ankle-foot orthosis is disclosed, along with steps for making and using same.

20 Claims, 12 Drawing Sheets

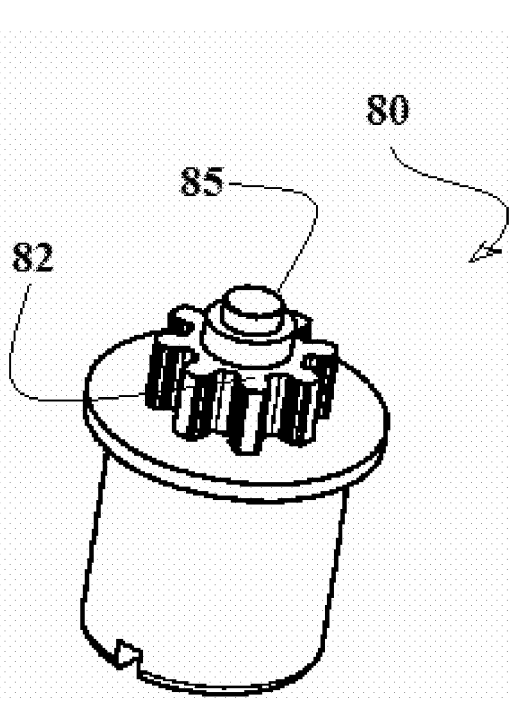
FIG. 8-1
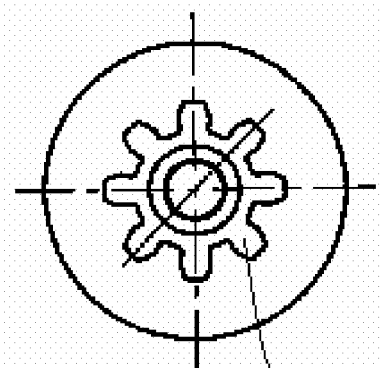
FIG. 8-3
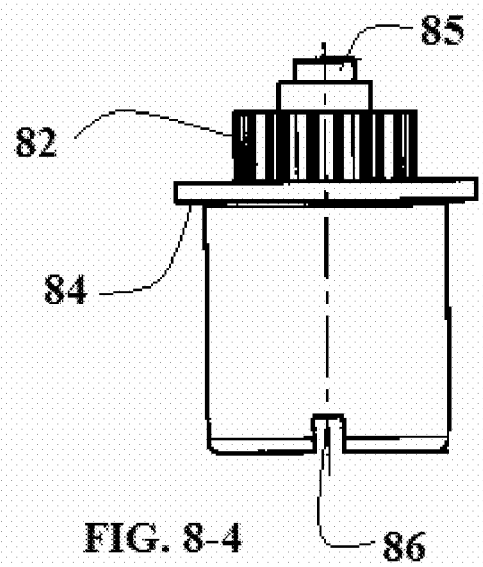
FIG. 8-4
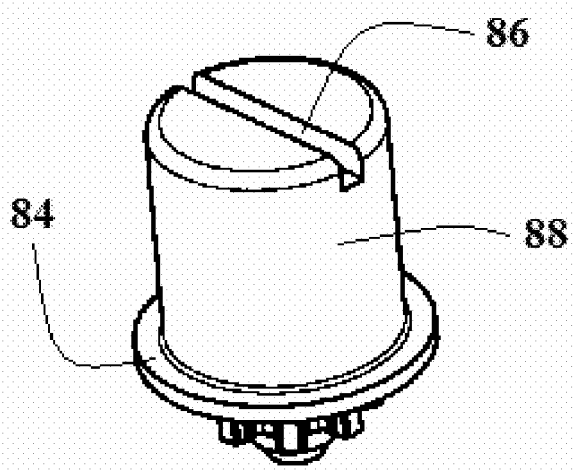
FIG. 8-2
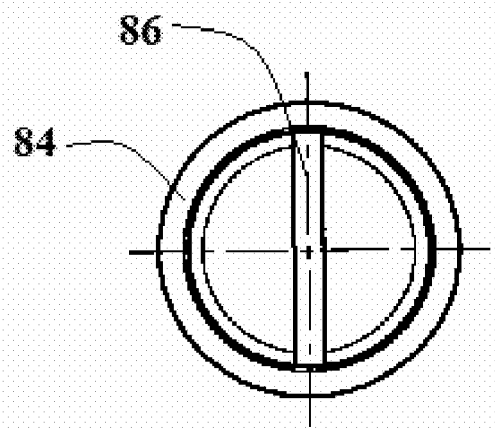
FIG. 8-5
FIG. 8

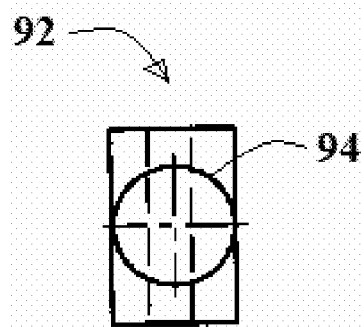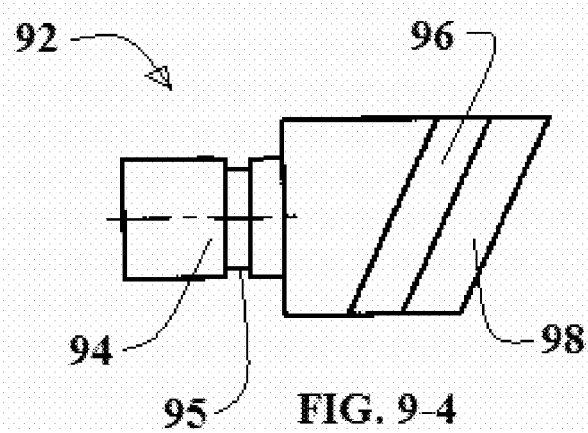
FIG. 9-5
FIG. 9-4
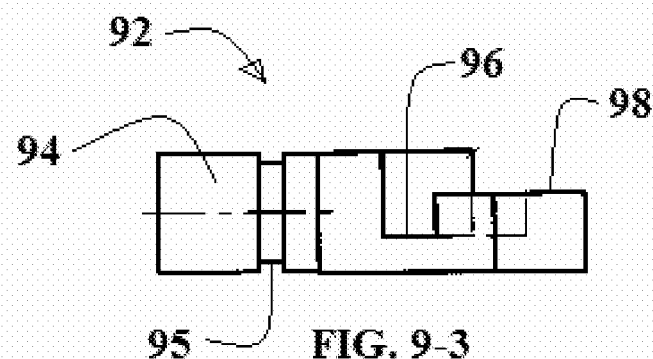
FIG. 9-3
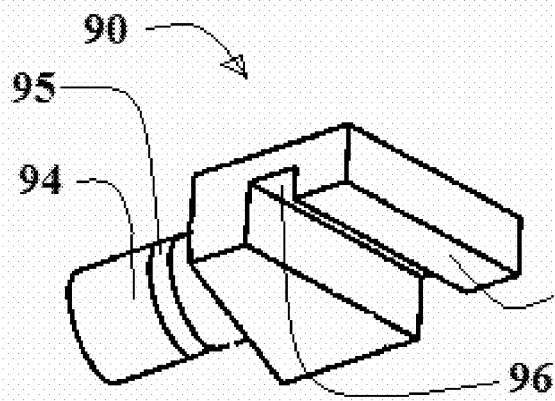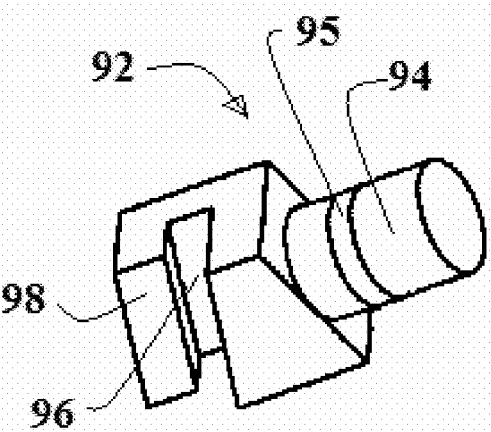
FIG. 9-1
FIG. 9-2
FIG. 9

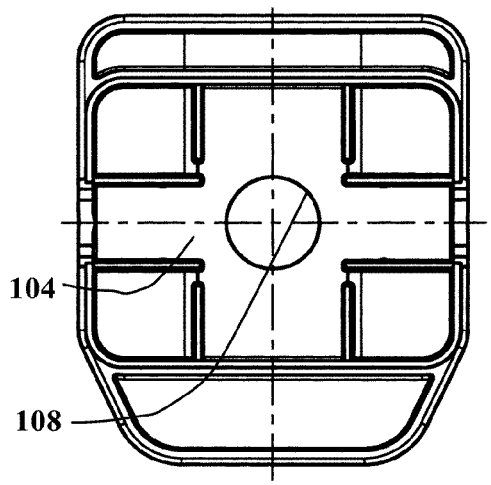
FIG. 10-5
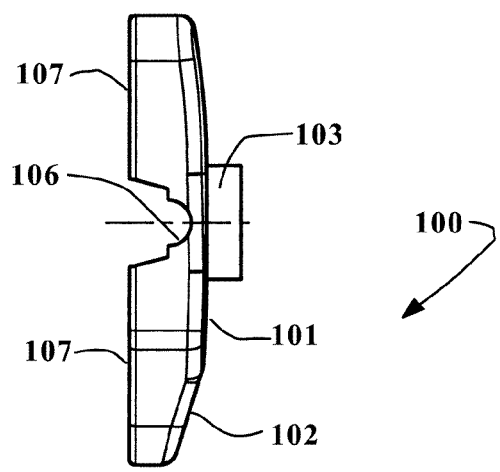
FIG. 10-6
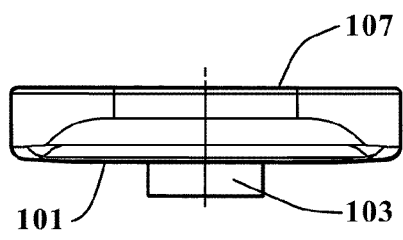
FIG. 10-4
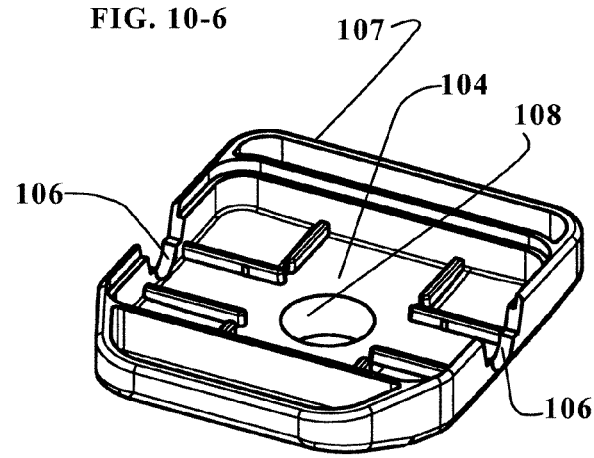
FIG. 10-2
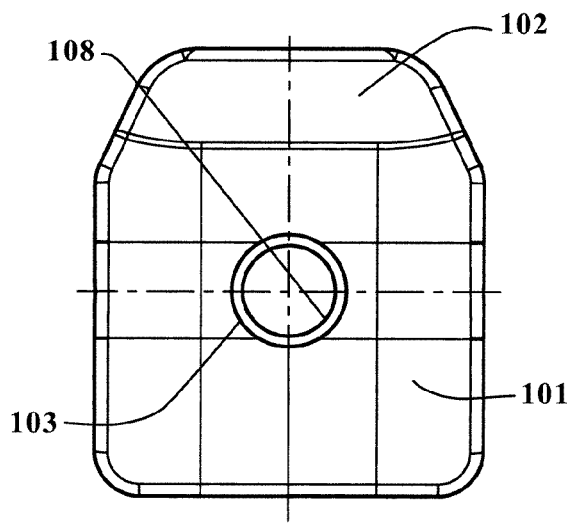
FIG. 10-3
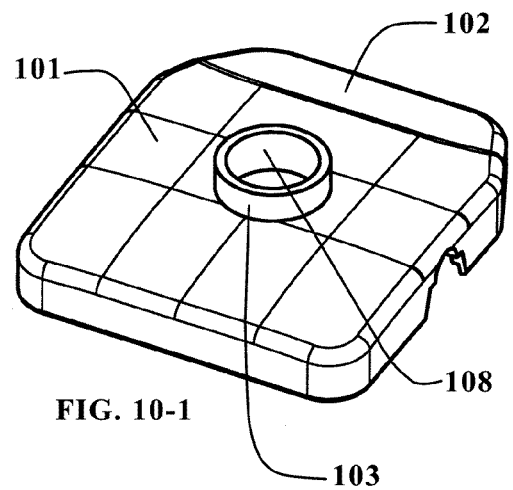
FIG. 10-1
FIG. 10

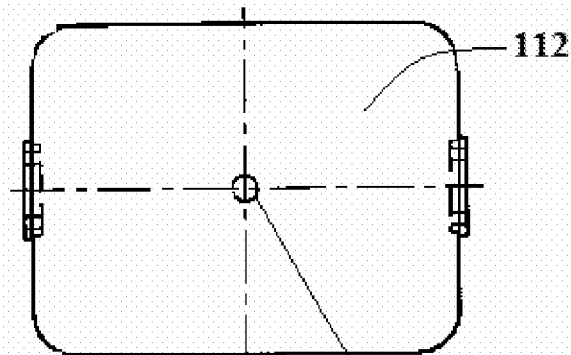
FIG. 11-5
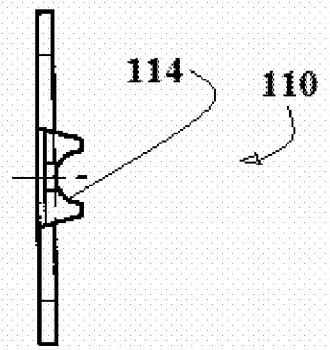
FIG. 11-6
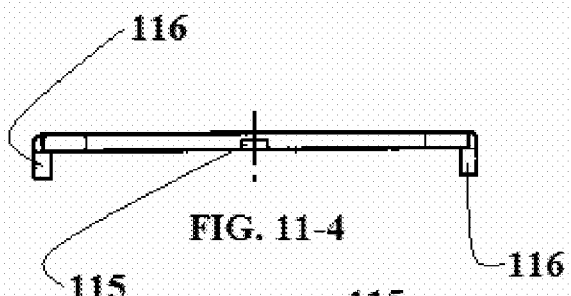
FIG. 11-4
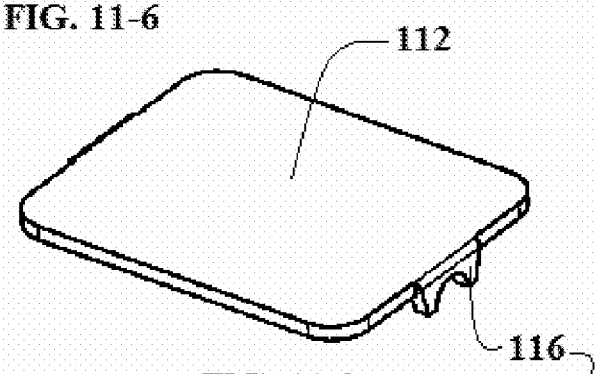
FIG. 11-2
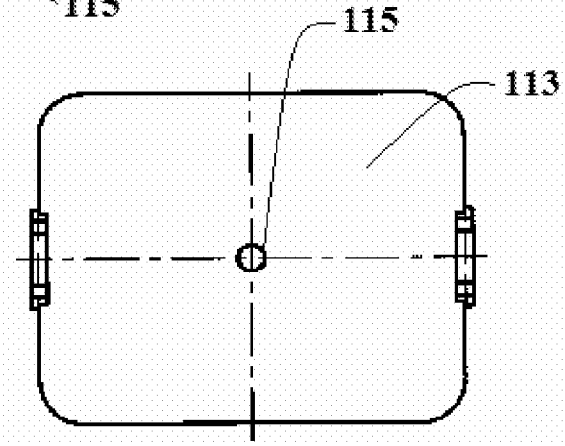
FIG. 11-3
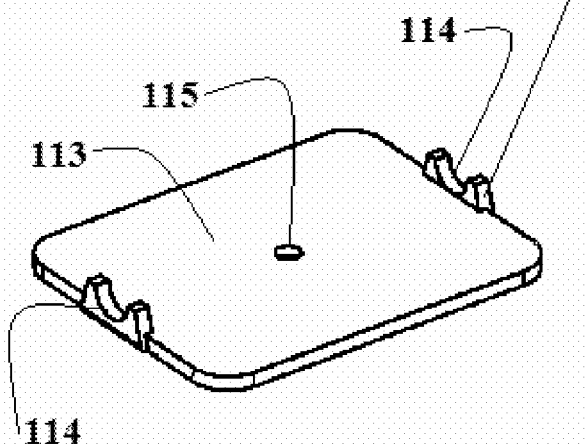
FIG. 11-1
FIG. 11

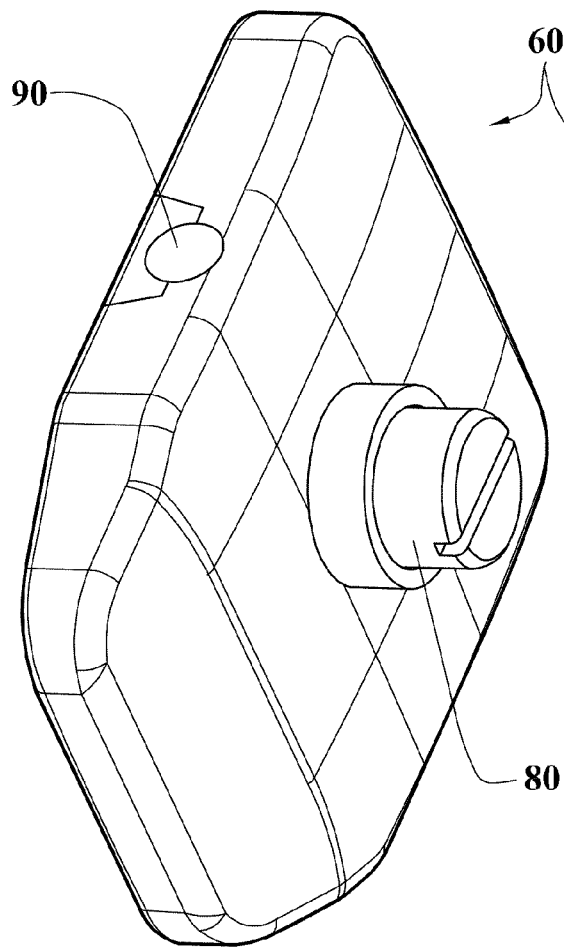
FIG. 12-1
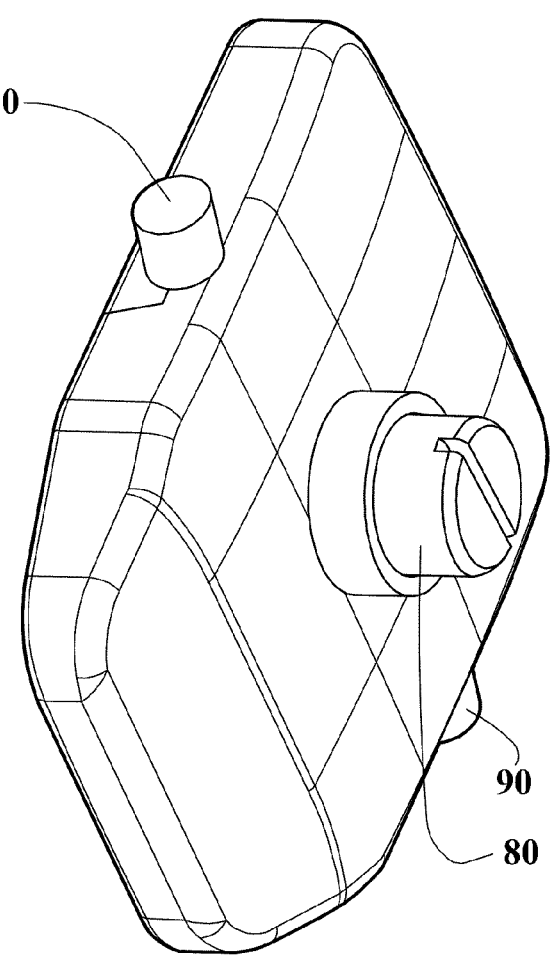
FIG. 12-2
FIG. 12

QUICK CONNECT APPARATUS AND METHOD

BACKGROUND

1. Field of the Invention

The present invention relates to a device and method for releasably connecting together two elements, such as two orthotic devices, or two elements of an orthotic device. More particularly, the invention relates to a quick connect apparatus that quickly and easily enables a user to attach and detach two devices or two elements of a device, such as the elements of a knee-ankle-foot orthosis.

2. Background of the Invention

Orthotic devices traditionally have been utilized to aid in supporting, guiding and limiting the range of motion of different joints in the human body, or in the case of prosthetic devices, to replace missing body joints and limbs or portions thereof. For example, if natural joints such as knees or ankles are congenitally impaired or become impaired due to disease or injury, an orthosis may be used to support the joints, and guide and limit their range of motion. Orthotic devices typically comprise one or more orthotic supporting members that support a limb or part of a limb, such as for example a foot, a leg, or a lower or upper portion of a leg. When more than one orthotic supporting member is used the members are typically connected with orthotic metal bars that may form a pivoting mechanical orthotic joint across, for example, the knee, elbow, wrist, hip, ankle, spine, torso or neck of a patient. Such orthotic metal bars are typically mounted on opposite sides of the orthotic supporting members and cannot usually be detached except by an orthotist using fabrication techniques. Orthotic devices are often custom fit specifically for an individual patient, such as by contouring orthotic supporting members and orthotic metal bars to a plaster mold of a patient's anatomy. Examples of such procedures are described in U.S. Pat. No. 6,171,535, the teachings of which are incorporated herein by reference.

In some cases a patient no longer needs part of their orthotic device, for instance where a patient with a knee-ankle-foot orthosis improves and requires only an ankle-foot orthosis. Alternatively, a patient with an ankle-foot orthosis may occasionally or temporarily need a knee-ankle-foot orthosis, for instance for certain physical activities. However, when orthotic metal bars are permanently or semi-permanently attached to the orthotic supporting members to create, for instance, a knee-ankle-foot orthosis, it is difficult and time consuming for the orthotist to later remove the various orthotic supporting members from the orthotic device. Because in the past they were not easily modified, patients have often required separate knee-ankle-foot and ankle-foot orthoses.

U.S. Pat. Nos. 6,129,689 and 6,736,567 to Dibello, both entitled Quick Connect Apparatus And Method For Orthotic And Prosthetics Devices, the teachings of which are incorporated herein by reference, are generally directed to a device for releasably connecting orthotic metal bars to orthotic supporting members. Each Dibello device includes two plate members attachable to different orthotic elements, and a slider plate that is movable between a first released position and a second locked position. The Dibello device also may include a stop to secure the slider plate in the locked position. While the Dibello device should theoretically be usable to allow a patient to releasably connect orthotic supporting members to his or her orthotic device, in practice the Dibello device has proven very difficult and tedious to implement and use, because it requires precise, simultaneous, three-dimensional alignment of complicated plate members. Specifically, two Dibello plate members must each be separately attached to orthosis metal bars, and then precisely aligned and connected with corresponding plate members attached to opposite sides of an orthotic supporting member. Such alignment and connection of the Dibello plate members is in practice very difficult even for a professional orthotist, due to the misalignment and dimensional variation inherent in custom fabrication, as well as normal flexing and deformation of the metal bars and polymer supporting members.

A need remains for a device and method of quickly and reliably attaching and detaching orthotic members to and from an orthotic device that can be performed easily, for instance by a patient. A need also exists for such a device and method allowing easy connection of orthotic members that is sturdy and reliable for the user of an orthotic device and will not inadvertently disconnect when the orthotic device is in use.

SUMMARY

For purposes of the present invention, the terms "orthotic elements" and "appliance elements" refer to orthotic bars, orthotic straps, cuffs or bands, prosthetic limbs or any other members which are desired to be connected in an orthotic or prosthetic device. Also as used herein, the term "appliance" shall mean an orthosis or orthotic device or a prosthesis or prosthetic device.

One aspect of the present invention relates to a quick connect device adapted to be affixed to a first element of an appliance for releasably connecting the first element of the appliance to a second element of the appliance, wherein the quick connect device comprises one or more engagement members that are drivable back and forth between a retracted position and an extended position by actuation of an actuatable member from a first position and a second position, the one or more engagement members being adapted to engage the second element of the appliance and connect the second element of the appliance to the first element of the appliance when the quick connect device is affixed to the first element of the appliance and the second element of the appliance is positioned adjacent the first element of the appliance and the actuatable member is actuated from the first position to the second position, where the one or more engagement members are further adapted to disengage the second element of the appliance and disconnect the second element of the appliance from the first element of the appliance when the actuatable member is then actuated from the second position to the first position. Alternatively, the quick connect device may comprise no fewer than two engagement members.

In accordance with one aspect of the invention the quick connect device may comprise a cam member adapted to drive the one or more engagement members back and forth between their retracted and extended positions when the actuatable member is actuated back and forth between its first position and second positions. The actuatable member may be adapted to drive the cam member back and forth between a lesser lift position and a greater lift position when the actuatable member is actuated back and forth between its first position and second positions.

Additionally, the quick connect device may comprise means to releasably lock the engagement members in an extended position.

One aspect of the present invention relates to an appliance with releasably connectable first and second elements, the appliance comprising a quick connect device affixed to the first element of the appliance for releasably connecting the first element of the appliance to the second element of the appliance, the quick connect device including one or more engagement members that are drivable back and forth between a retracted position and an extended position by actuation of an actuatable member from a first position and a second position, the one or more engagement members being releasably engagable with the second element of the appliance to connect the second element of the appliance to the first element of the appliance when the second element of the appliance is positioned adjacent the first element of the appliance and the actuatable member is actuated from the first position to the second position, the one or more engagement members being disengagable from the second element of the appliance to disconnect the second element of the appliance from the first element of the appliance when the actuatable member is actuated from the second position to the first position.

In accordance with one aspect of the invention the appliance may comprise a knee-ankle-foot orthosis.

In accordance with one aspect of the invention the first element of the appliance may be part of an ankle-foot orthosis.

In accordance with one aspect of the invention the appliance may comprise a prosthetic device.

One aspect of the present invention relates to a method of releasably connecting first and second elements of an appliance, the method comprising affixing a quick connect device to the first element of the appliance for releasably connecting the first element of the appliance to the second element of the appliance, the quick connect device including one or more engagement members that are drivable back and forth between a retracted position and an extended position by actuation of an actuatable member from a first position and a second position, the one or more engagement members being releasably engagable with the second element of the appliance to connect the second element of the appliance to the first element of the appliance when the second element of the appliance is positioned adjacent the first element of the appliance and the actuatable member is actuated from the first position to the second position, the one or more engagement members being disengagable from the second element of the appliance to disconnect the second element of the appliance from the first element of the appliance when the actuatable member is actuated from the second position to the first position; positioning the actuatable member such that the one or more engagement members are in the retracted position; and positioning the second element of the appliance adjacent the first element of the appliance and releasably connecting the first and second elements of the appliance by positioning the actuatable member such that the one or more engagement members are in the extended position and engaging the second element of the appliance.

In accordance with one aspect of the invention the method of releasably connecting first and second elements of an appliance further may further comprise the step of disconnecting the second element of the appliance from the first element of the appliance by positioning the actuatable member such that the one or more engagement members are in the retracted position and disengaged from the second element of the appliance.

BRIEF DESCRIPTION OF THE DRAWINGS

FIG. 8 is a series of views of an example actuatable member of the example quick connect device mechanism of FIG. 6, with FIG. 8-1 being a bottom perspective view, FIG. 8-2 being a top perspective view, FIG. 8-3 being a bottom view, FIG. 8-4 being a side view, and FIG. 8-5 being a top view thereof;

FIG. 9 is a series of views of example engagement members of the example quick connect device mechanism of FIG. 6, with FIG. 9-1 being a bottom perspective view of a left-side engagement member, FIG. 9-2 being a bottom perspective view of a right-side engagement member, FIG. 9-3 being a side view of the member of FIG. 9-2, FIG. 9-4 being a bottom view of the member of FIG. 9-2, and FIG. 9-5 being an end view of the member of FIG. 9-2;

FIG. 10 is a series of views of an example housing member of the example quick connect device mechanism of FIG. 6, with FIG. 10-1 being a top perspective view, FIG. 10-2 being a bottom perspective view, FIG. 10-3 being a top view, FIG. 10-4 being a side view, FIG. 10-5 being a bottom view, and FIG. 10-6 being a side view thereof;

FIG. 11 is a series of views of an example housing cover member of the example quick connect device mechanism of FIG. 6, with FIG. 11-1 being a top perspective view, FIG. 11-2 being a bottom perspective view, FIG. 11-3 being a top view, FIG. 11-4 being a side view, FIG. 11-5 being a bottom view, and FIG. 11-6 being a side view thereof;

FIG. 12 is a series of views of the example quick connect device mechanism of FIG. 6, with FIG. 12-1 being a top perspective view showing the engagement members in a retracted position, and FIG. 12-2 being a top perspective view thereof showing the engagement members in an extended position.

DETAILED DESCRIPTION

While the quick-connect apparatus and method described below will be described with respect to ankle-foot and knee-ankle-foot orthoses, the principles will apply to other appliances as well.

Figure 1:
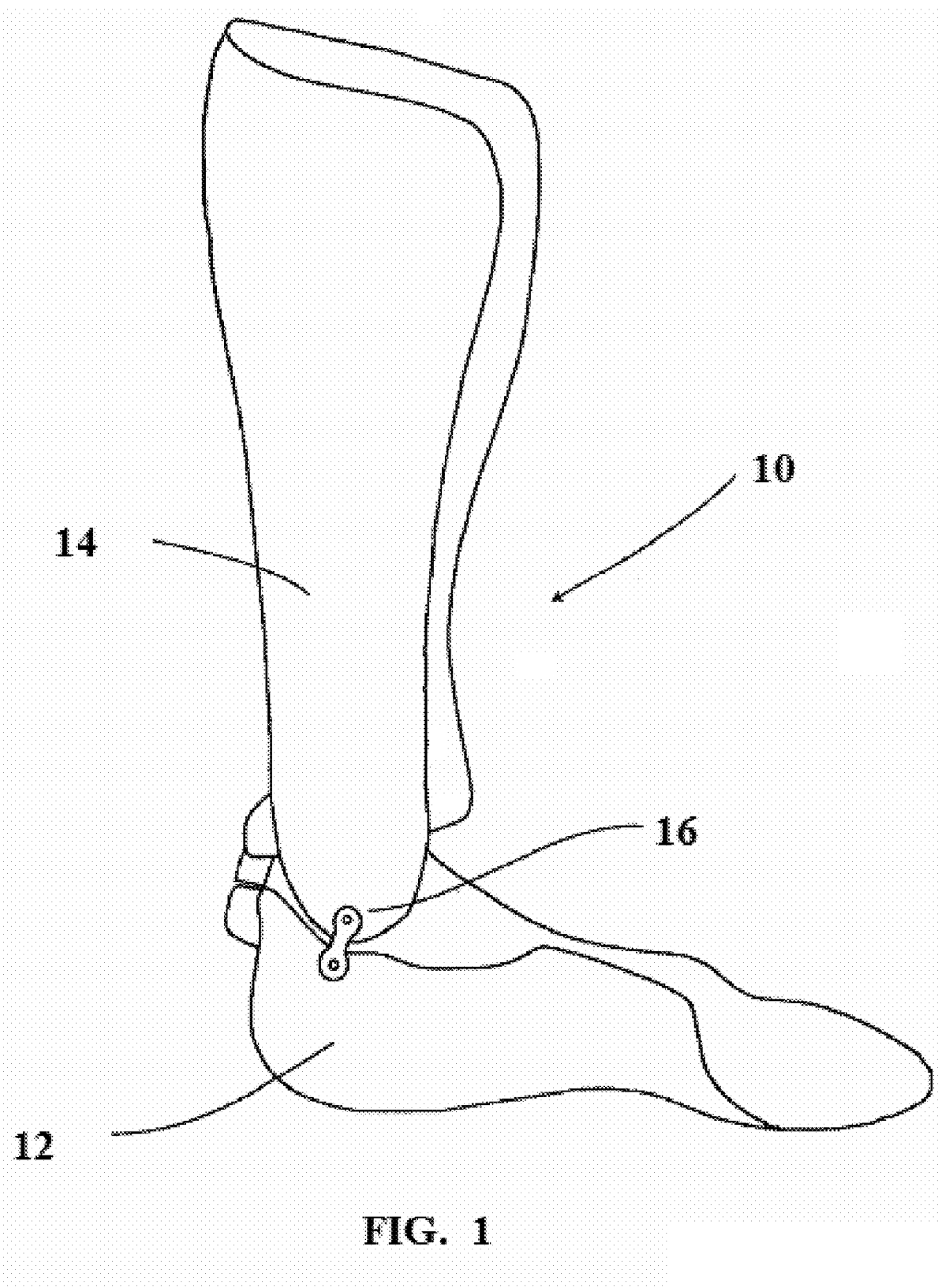
FIG. 1 is a perspective view of an example prior art ankle-foot orthosis ("AFO") with an ankle joint.
Figure 2:
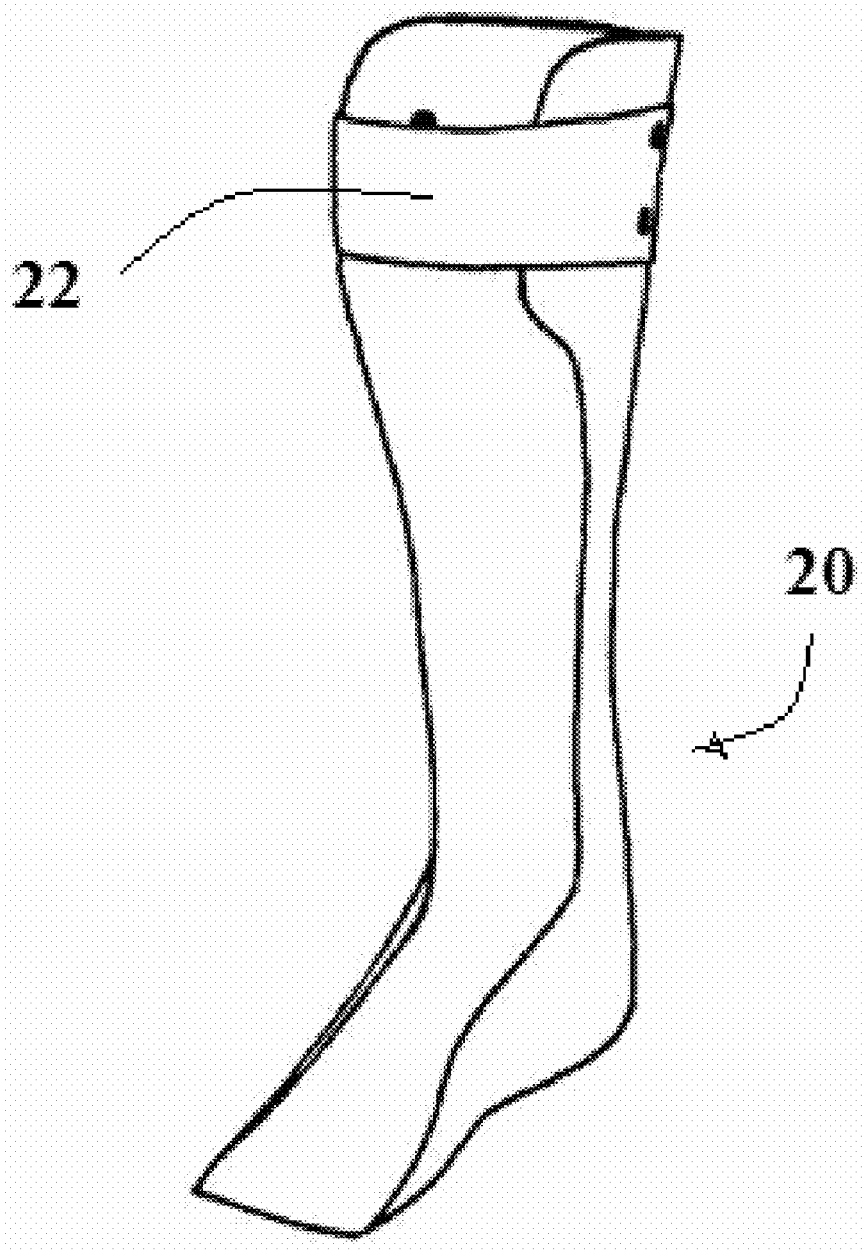
FIG. 2 is a perspective view of an example prior art ankle-foot orthosis ("AFO") without an ankle joint.

Referring to FIG. 1, an example prior art ankle-foot orthosis 10 ("AFO") is shown including a foot support element 12, a calf support element 14, and an ankle joint 16. Alternatively, an ankle-foot orthosis 20 can be one-piece or otherwise omit an ankle joint, as shown in FIG. 2. Orthoses such as an ankle-foot orthosis typically include one or more straps 22. Other example straps are shown in more detail in U.S. Pat. No. 7,018,352, all the teachings of which are incorporated herein by reference.

Figure 3:
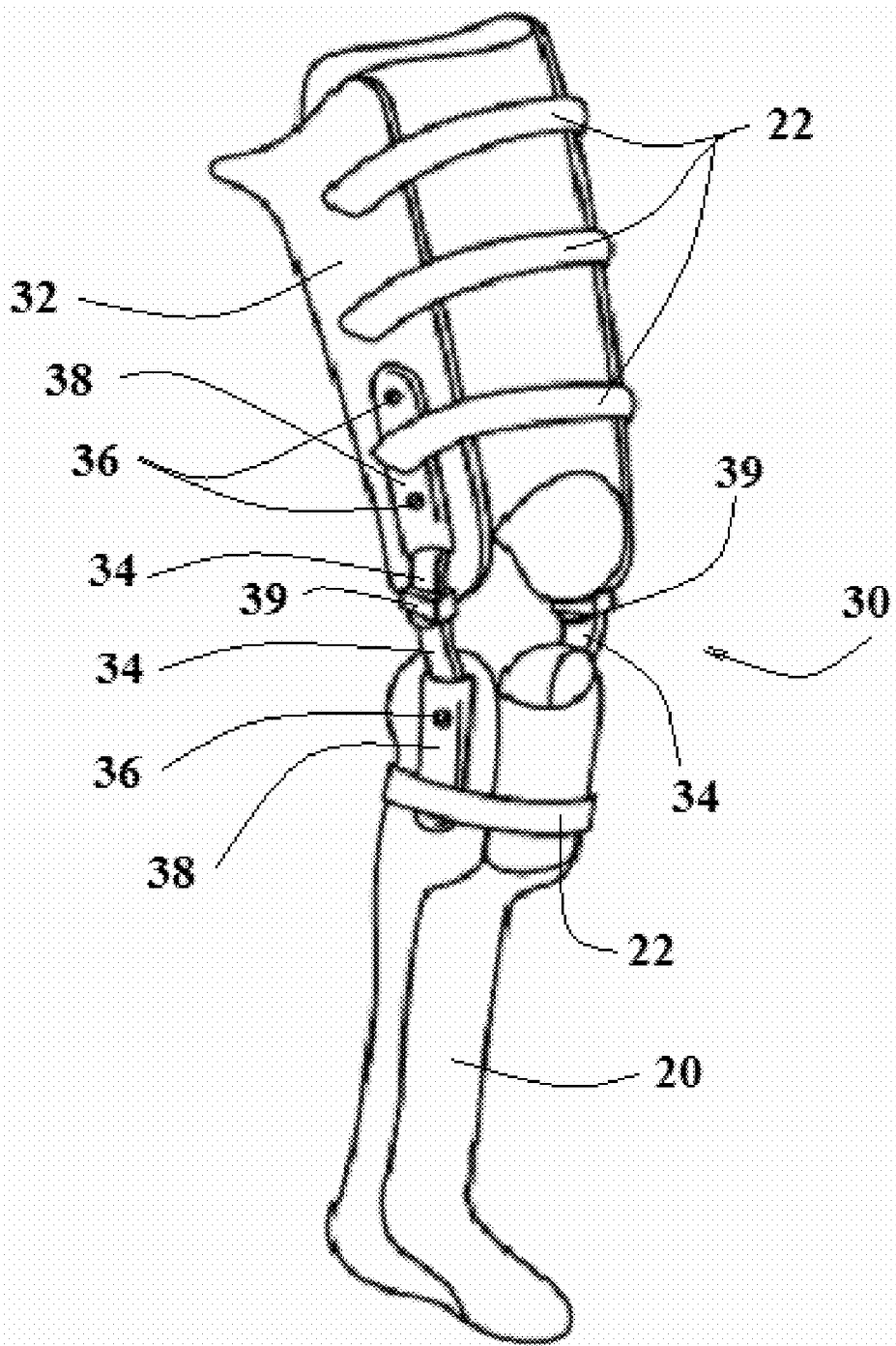
FIG. 3 is a perspective view of an example prior art knee-ankle-foot orthosis ("KAFO") without an ankle joint.

FIG. 3 depicts an example prior art knee-ankle-foot orthosis 30 ("KAFO"), comprising a one-piece ankle-foot orthosis 20 connected to a thigh support member 32 by metal bars 34 that are permanently or semi-permanently affixed to first and second sides of orthosis 20 and support member 32 by fasteners 36 and over-lamination areas 38, which at least partially encapsulate the metal bars 34. Straps 22 for holding a patient's leg (not shown) into the orthosis 30 are also depicted. The metal bars 34 may include joints 39 on each side to allow the ankle-foot orthosis 20 to pivot in a controlled manner relative to the thigh support member 32, as is known in the art.

Figure 4:
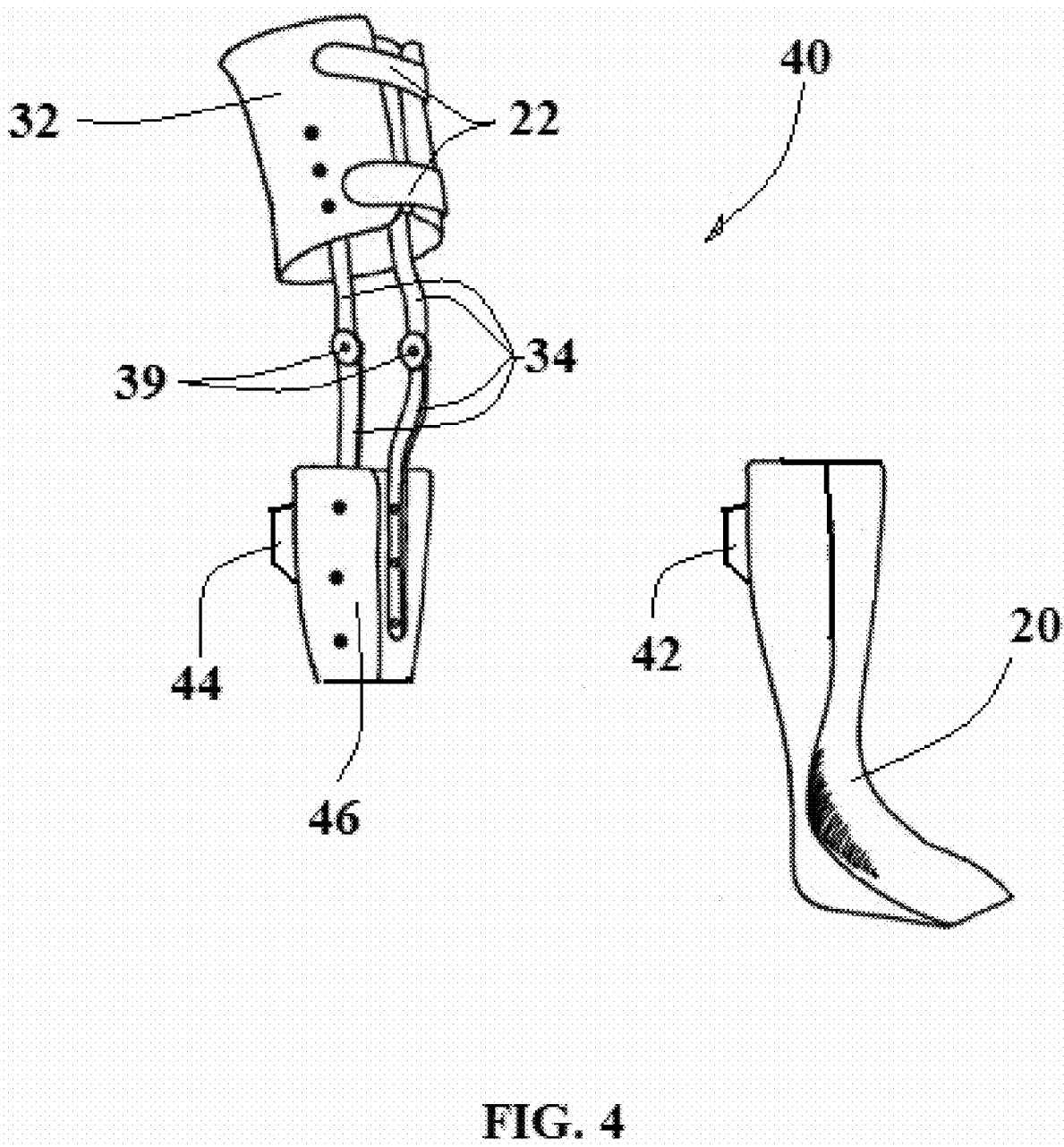
FIG. 4 is a perspective view of an example appliance according to the present invention showing the quick connect device in the unlocked position.

An example embodiment 40 will now be discussed with reference to FIGS. 4, 5, 6, 10 and 12. As an example first element of an appliance, FIG. 4 depicts a one-piece ankle-foot orthosis member 20 with an example quick connect device mechanism 60 (shown in FIGS. 6 and 12) attached to and at least partially encapsulated in the body of orthosis member 20 at location 42, for instance by over-lamination. In one embodiment the example quick connect device mechanism 60 is completely encapsulated in the body of orthosis member 20 at location 42, except openings are provided to allow a user to access actuatable member 80 and to allow engagement members 90 to be extended from retracted positions FIG. 12-1 to extended positions FIG. 12-2. Alternatively, an example quick connect device mechanism 60 can be attached to orthosis member 20 with glue, fasteners, or any other suitable fastening means at or near location 42, instead of or in addition to encapsulation in the body of the orthosis member 20. In one embodiment the example quick connect device mechanism 60 is positioned on or in the orthosis member 20 at or near location 42 with the bottom 110 of the housing 100 positioned toward the leg (not shown) of the wearer of the orthosis member 20, with the actuatable member 80 positioned away from the leg of the wearer, and with the tapered portion 102 of the housing 100 positioned upward to provide an outer profile decreasing in size as it extends upward toward the back of the wearer's knee. When so oriented the tapered portion 102 may provide additional clearance with respect to seating in which the orthosis wearer may sit. Alternatively the various elements of a quick connect device can be positioned in any suitable location and orientation.

Figure 5:
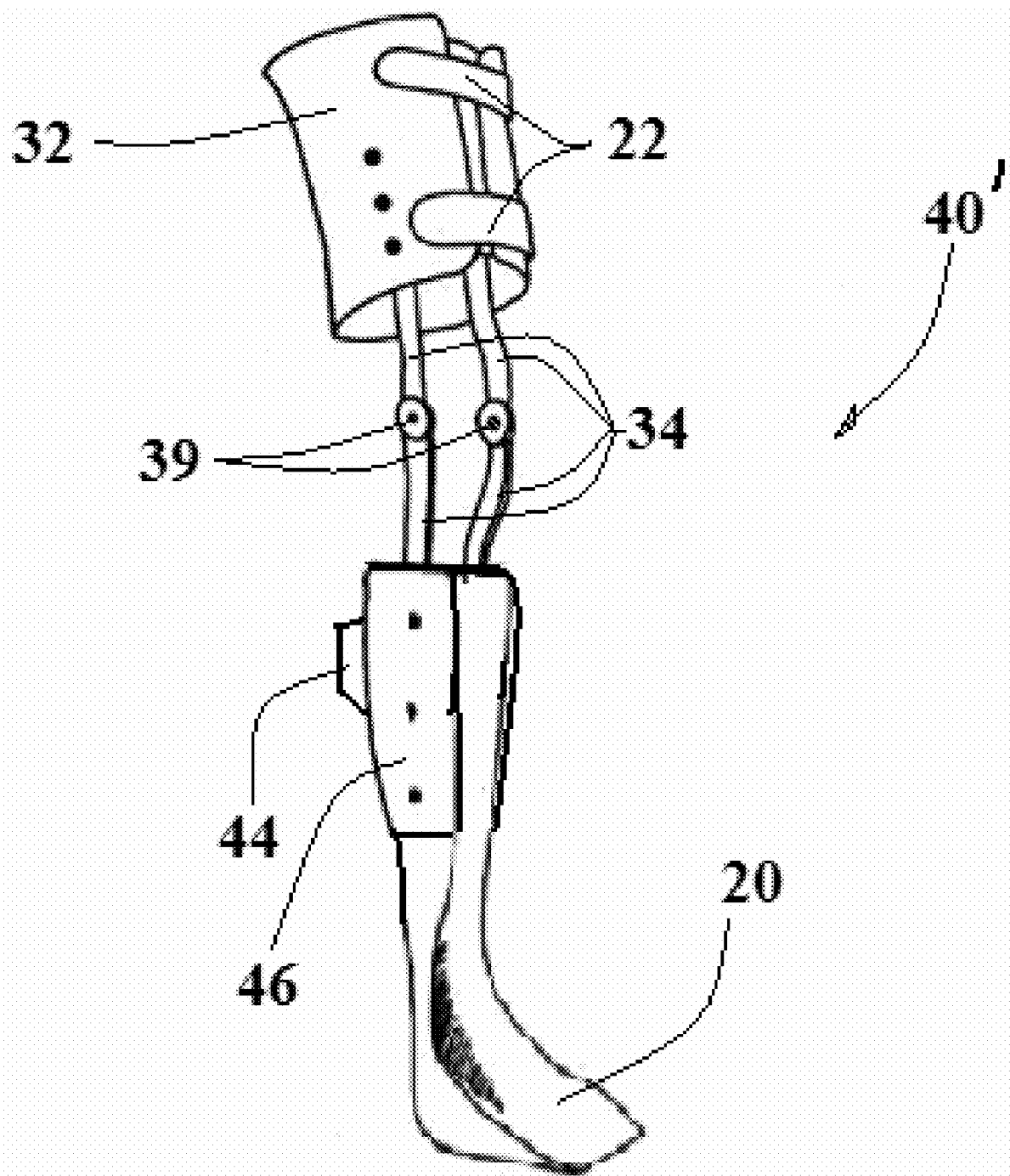
FIG. 5 is a perspective view of the example appliance of FIG. 4 showing the quick connect device in the locked position.

Also shown in FIG. 4 is a second element of an appliance, in this example a calf support element 46. Calf support element 46 may be connected to thigh support element 32 by orthotic metal bars 34 that may include joints 39, as described above with respect to prior art connections of orthotic metal bars to other orthotic elements. In the example shown, calf support element 46 is contoured to be placed against and fit closely around the upper exterior of ankle-foot orthosis member 20. In this example calf support element 46 includes a receiver portion 44 adapted to fit around the example quick connect device mechanism 60. The receiver portion 44 may include an opening to allow a user to access actuatable member 80 when calf support element 46 is placed against ankle-foot orthosis member 20 as shown in FIG. 5. The receiver portion 44 may further include recesses, detents, or openings adapted to receive and engage engagement members 90 when calf support element 46 is placed against ankle-foot orthosis member 20 as shown in FIG. 5 and engagement members 90 are extended from retracted positions FIG. 12-1 to extended positions FIG. 12-2 as explained herein. While the above embodiment is described with an example quick connect device mechanism 60 attached to orthosis member 20 and engaging calf support element 46 at receiver portion 44, in an alternative embodiment a quick connect device could be attached to calf support element 46 and adapted to engage orthosis member 20.

FIG. 5 depicts the first appliance element 20 and second appliance element 46 of FIG. 4 attached to form a knee-ankle-foot orthosis 40'. This attachment can easily be accomplished by a user, such as a patient wearing the appliance or any other person, by placing the calf support element 46 against ankle-foot orthosis member 20 as shown in FIG. 5, and causing engagement members 90 to be extended from retracted positions FIG. 12-1 to extended positions FIG. 12-2, thereby engaging engagement members 90 with corresponding and adjacent receiver portion 44 of calf support element 46. Engagement members 90 can be caused to be extended from retracted positions FIG. 12-1 to extended positions FIG. 12-2 by actuating actuatable member 80 of quick connect device 60 as discussed below. Knee-ankle-foot orthosis 40' can then easily be changed back to a stand-alone ankle-foot orthosis 20 by actuating actuatable member 80 of quick connect device 60 to cause engagement members 90 to be retracted from extended positions FIG. 12-2 to retracted positions FIG. 12-1, and removing first appliance element 20 from second appliance element 46.

Figure 6:
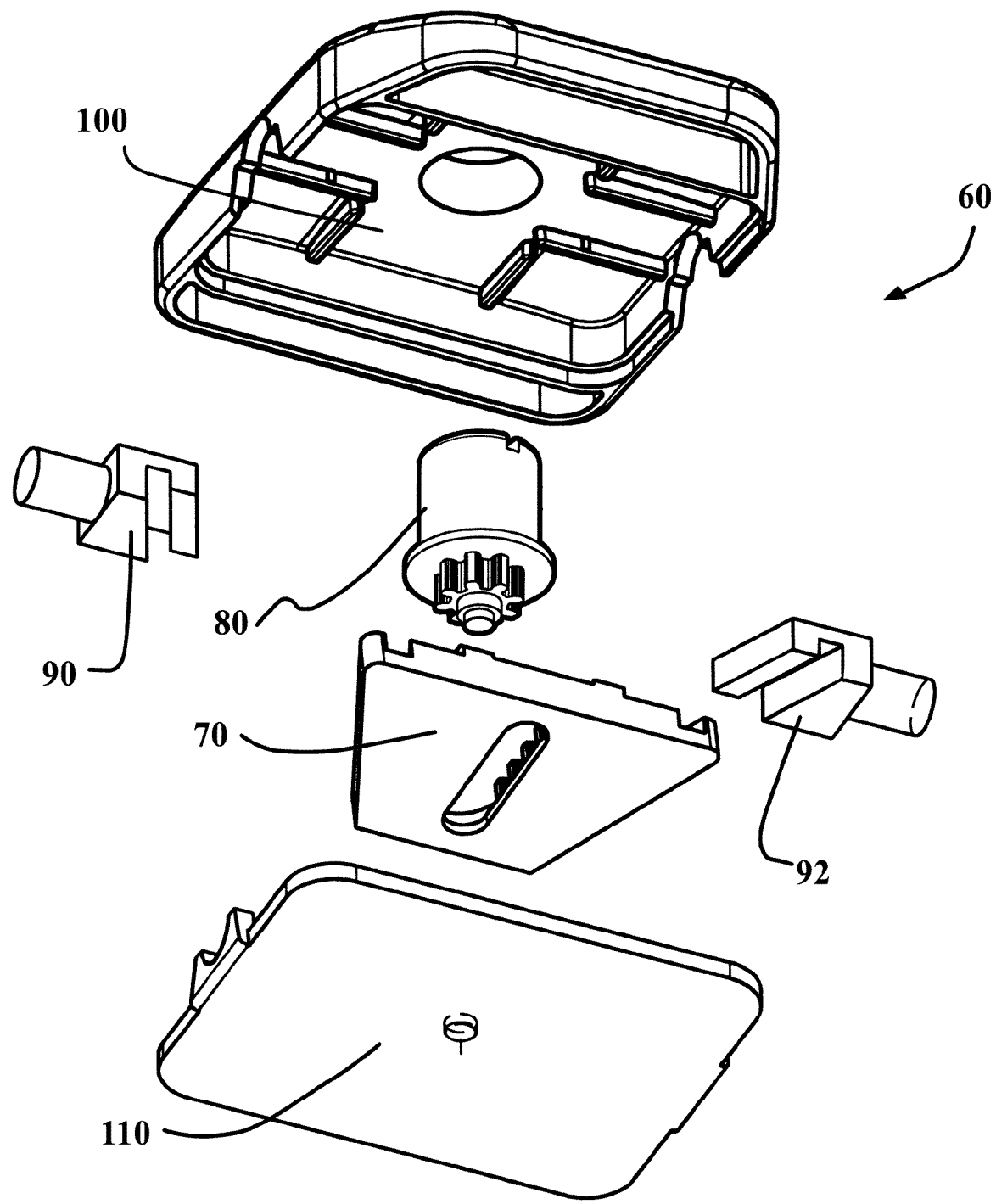
FIG. 6 is a perspective exploded view of an example quick connect device mechanism according to the present invention.
Figure 7:
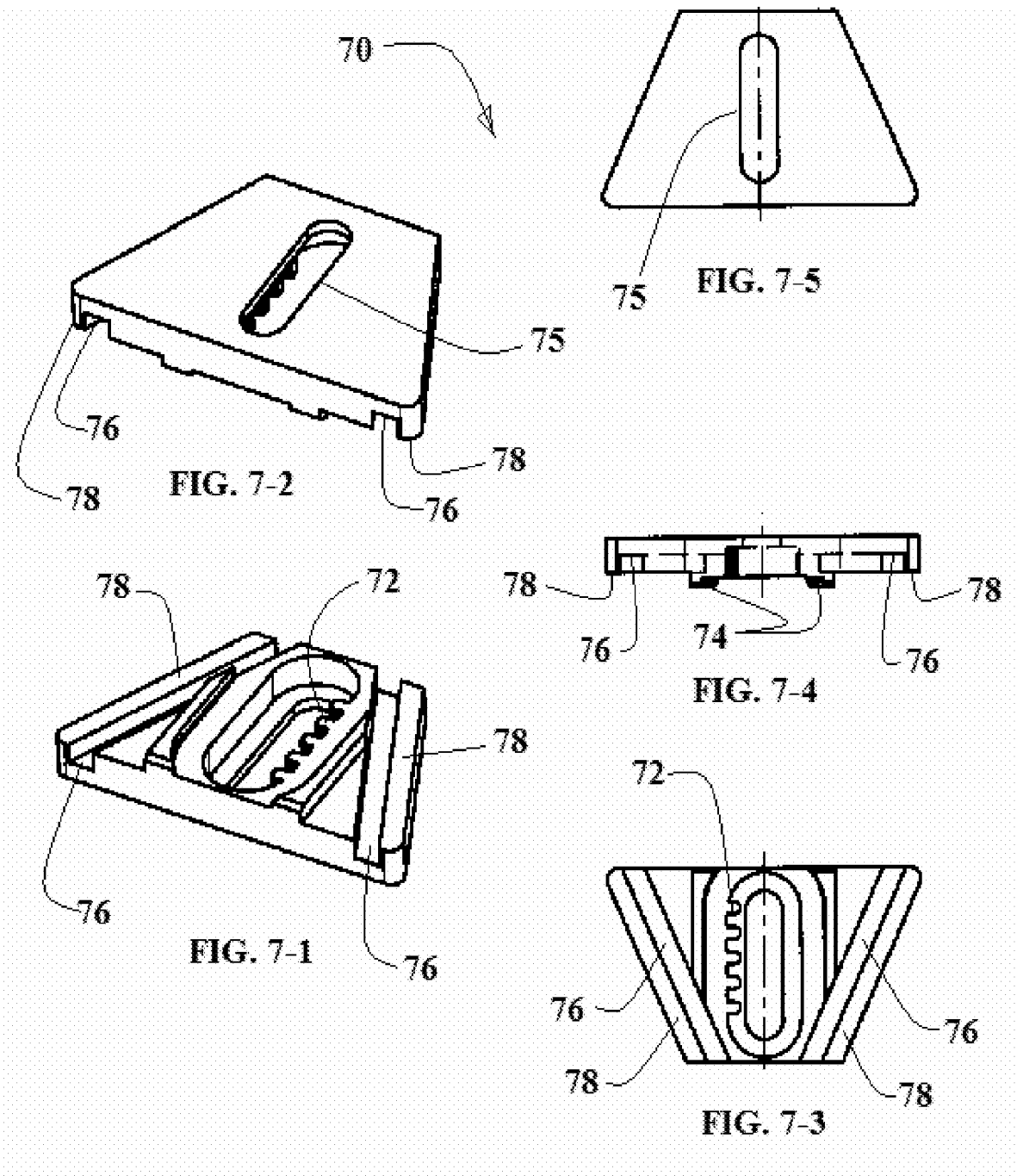
FIG. 7 is a series of views of an example cam member of the example quick connect device mechanism of FIG. 6, with FIG. 7-1 being a top perspective view, FIG. 7-2 being a bottom perspective view, FIG. 7-3 being a top view, FIG. 7-4 being a side view, and FIG. 7-5 being a bottom view thereof.

The components of an example quick connect device 60 will now be described. FIG. 6 depicts an exploded view of an example quick connect device 60, including housing 100 and housing bottom 110 encompassing and supporting cam member 70, actuatable member 80, and engagement members 90. As shown in FIG. 7, example cam member 70 includes a rack of gear teeth 72, an interface surface 74 that interfaces with actuatable member 80, a pilot slot 75 that interfaces with actuatable member 80, and cam grooves 76 and cam ridges 78 that interface with engagement members 90, 92. When assembled as shown in quick connect device 60, cam member 70 interfaces with and is driven by example actuatable member 80 shown in FIG. 8. Example actuatable member 80 includes a pinion of gear teeth 82 that are adapted to mesh with cam member gear teeth 72, a shoulder 84 that interfaces with and is axially restrained in one direction by inner surface 104 of housing 100 (shown in FIG. 10), a pilot protrusion 85 that interfaces with and is located by pilot slot 75 in cam member 70, and a slot 86 adapted to interface with a flat screw driver, or a coin, such as a penny, nickel, dime, or quarter. Slot 86 could alternatively be replaced by any suitable structure, such as, for example, an external hex shape to be driven by a wrench, or a phillips-style interface, or a torx-style interface, or an allen-style interface. Example actuatable member 80 further includes an outer-diameter bearing surface 88 which interfaces with and is located by inner-diameter bearing surface 108 in housing 100. Example quick connect device 60 further includes left and right, or first side and second side, engagement members 90 and 92 as shown in FIG. 9. Left and right, or first side and second side, engagement members 90 and 92 are in this example mirror images of each other; accordingly, their features will be described with respect to right, or second side engagement member 92. Engagement members 90, 92 include engagement surfaces 94 that slidably interface with and are located by surfaces 106 of housing 100 and surfaces 114 of housing bottom 110. Engagement surfaces 94 are further adapted to engage receiver portion 44 of calf support element 46, for instance by having holes (not shown) in receiver portion 44 dimensionally corresponding to engagement members 90, 92 as located by surfaces 106 of housing 100 and surfaces 114 of housing bottom 110 when first appliance element 20 and second appliance element 46 of FIG. 4 are attached to form a knee-ankle-foot orthosis 40' as shown in FIG. 5. Engagement members 90, 92 may further include grooves 95 that interface with and catch on surfaces 106 of housing 100 and surfaces 114 of housing bottom 110 when engagement members 90, 92 are in extended positions FIG. 12-2. This interface of grooves 95 with housing 100 and housing bottom 110 creates a locking effect, effectively locking the engagement members 90, 92 in extended positions FIG. 12-2 such that first appliance element 20 does not inadvertently disconnect from appliance element 46 of FIG. 4. This locking effect may be overcome, and the mechanism un-locked, by applying extra force to actuatable member 80, to pop surfaces 106 and 114 out of grooves 95. Engagement members 90, 92 include engagement slots 96 and engagement ridges 98 that slidably interface with corresponding cam ridges 78 and cam grooves 76, respectively, of cam member 70. As shown in FIG. 10, example housing 100 includes a top surface 101, a tapered surface 102 that tapers away from top surface 101, a raised boss 103 extending upward from the top surface 101 and designed to extend through overlamination material at least partially encapsulating connecting device 60 and connecting it to first appliance element 20, an inner surface 104, surfaces 106 to guide and engage members 90, 92, bottom edges 107, and an inner-diameter bearing surface 108 for locating and interfacing with actuatable member 80. Example housing bottom 110 is shown in FIG. 11, and snap-fits between bottom edges 107 of housing 100, and includes a bottom surface 112, a top surface 113, surfaces 114 on ears 116 to guide and engage members 90, 92, and a pilot hole or recess 115 to engage and locate pilot protrusion 85 of actuatable member 80. The various components of quick connect device 60 discussed above may each be made from any suitable material, such as nylon 6/6 or any other suitable polymer or metal, and may be formed by any combination of machining, plastic injection molding, compression molding, vacuum molding, or any other suitable manufacturing process.

Operation of example quick connect device mechanism 60 will now be described. A user actuates actuatable member 80 by rotating it, for instance by engaging a screw driver or a coin in slot 86. In other example mechanisms actuatable member 80 may be replaced by one or more switches, latches, buttons, levers, or any suitable mechanism adapted to drive one or more engagement members 90, 92. While two engagement members 90, 92 are shown in this example, in other embodiments one engagement member may be used, or three or more engagement members may be used. When actuatable member 80 is rotated in a first or second rotational direction, gear teeth 82 drive cam member gear teeth 72, slidably translating cam member 70 in a first or second axial direction within housing 100. When cam member 70 is translated in a first or second axial direction, engagement slots 96 and engagement ridges 98 of engagement members 90, 92 slidably interface with corresponding axially angled cam ridges 78 and cam grooves 76, respectively, of cam member 70, which then vary between lesser and greater lifts as cam member 70 is translated axially, and which cause engagement surfaces 94 of engagement members 90, 92 to slide past surfaces 106 of housing 100 and surfaces 114 of housing bottom 110 a distance corresponding to the change in lift of the cam member 70. When actuatable member 80 is rotated in a first rotational direction, engagement surfaces 94 of engagement members 90, 92 slide past surfaces 106 of housing 100 and surfaces 114 of housing bottom 110 and extend to an extended position as shown in FIG. 12-2. When fully extended or sufficiently extended, grooves 95 in engagement members 90, 92 engage with surfaces 106 of housing 100 and surfaces 114 of housing bottom 110, locking the mechanism in the extended position as shown in FIG. 12-2. Engagement members 90, 92 may then be retracted by rotating actuatable member 80 in a second rotational direction, first applying sufficient force to disengage surfaces 106 of housing 100 and surfaces 114 of housing bottom 110 from grooves 95, and then causing engagement surfaces 94 of engagement members 90, 92 to slide past surfaces 106 of housing 100 and surfaces 114 of housing bottom 110 to a retracted position as shown in FIG. 12-1.

An example fabrication technique will now be discussed. A KAFO (Knee Ankle Foot Orthosis) cast or mold is created based on the shape of a patient's limb and may be fully modified and screened to the practitioner's expectations. Once a cast or mold is made, locate an area on the mold corresponding to where the quick connect device mechanism 60 will be located and trace with an indelible pencil, approximately three inches distal from the fibular head. An orthotist may use judgment on pediatric applications as they may vary. Using a flat sure form make a flat surface (using indelible marks as guide) on which to place the quick connect device mechanism 60 (screen smooth after satisfied with the way the box sits on the mold). Once the mold is fully shaped, seal it to reduce moisture, then place a nylon covering, such as nylon leg hosiery, over the mold. Later when a vacuum is applied, the vacuum will be communicated between the fibers and through the openings in the nylon material. Next, use plastic such as a trash bag to wrap and seal the nylon-covered upper thigh area of the KAFO, from the top just passed the knee center. Seal the ends of plastic material to the nylon with black electrical tape, covering several inches of nylon with the tape, and seal the other end of the plastic material to a vacuum source. Apply a small amount of spray adhesive to the nylon material where the quick connect device mechanism 60 will be placed, and place the quick connect device mechanism 60 there. Heat up 1/16 inch thick polyethylene, at least 7 inch by 7 inch in size, in an oven until it becomes substantially transparent, for instance about 18 minutes at 350 degrees Fahrenheit. Then remove the heated polyethylene from the oven and stretch it over the area on the mold where the quick connect device mechanism 60 is placed. The heated polyethylene may contact the quick connect device mechanism 60, the nylon, the mold, and the black electrical tape, but may not touch the plastic bag material. The polyethylene may be stretched around the mold until it thins down to approximately 1/32 inch thick, and it should be compressed together to form an airtight enclosure around the mold. Apply a strong vacuum to the interior of the plastic bag, which vacuum is then communicated through the nylon hosiery, under the electrical tape, and under the heated polyethylene that encloses the mold. The vacuum will then suck the heated polyethylene tightly to the nylon hosiery-covered mold, over and encapsulating the quick connect device mechanism 60. After the material cools somewhat but while it is still hot to the touch, use a razor blade to cut the polyethylene away from the locations of engagement members 90, 92 so that they may extend as shown in FIG. 12-2, and grind away the polyethylene material covering the actuatable member 80 so that it may be actuated. After the material cools to substantially room temperature, the foregoing steps are repeated by heating, stretching, and vacuum-forming a second layer of polyethylene over the first layer of polyethylene at the location of the quick connect device mechanism 60, while the engagement members 90, 92 are extended as shown in FIG. 12-2. This will form the corresponding engagement areas for engagement members 90, 92 in the second layer of polyethylene. The second layer of polyethylene material covering the actuatable member 80 must also be ground away so that it may be actuated. In the present example discussed herein, the first layer of polyethylene will form the ankle-foot orthosis 20, including protrusion 42 encapsulating quick connect device mechanism 60, and the second layer of polyethylene will form calf support element 46 including receiver portion 44 form-fitted to fit around protrusion 42 ankle-foot orthosis 20. After the material cools, excess material is cut away and typical orthosis hardware is added as is known in the art to produce an appliance as shown in FIGS. 4 and 5.

While the foregoing invention has been described with reference to its preferred embodiments, various alterations and modifications will occur to those skilled in the art. All such alterations and modifications are intended to fall within the scopes of the appended claims.

What is claimed is:

1. A quick connect device adapted to be at least partially encapsulated within a first body-supporting element of an orthotic or prosthetic appliance, the first body-supporting element adapted to support and at least partially surround a portion of a wearer's body, for releasably connecting the first body-supporting element of the appliance to a second element of the appliance, where the second element is contoured to be placed adjacent and fit closely around that portion of the first body-supporting element where the quick connect device is at least partially encapsulated within the first body-supporting element, the quick connect device comprising:

one or more engagement members that are drivable back and forth between a retracted position and an extended position by actuation of an actuatable member between a first position and a second position, the one or more engagement members being adapted to engage the second element of the appliance and connect the second element of the appliance to the first element of the appliance when the quick connect device is at least partially encapsulated within the first body-supporting element of the appliance and the second element of the appliance is positioned adjacent and fit closely around that portion of the first body-supporting element where the quick connect device is at least partially encapsulated within the first body-supporting element and the actuatable member is actuated from the first position to the second position, the one or more engagement members being further adapted to disengage the second element of the appliance and disconnect the second element of the appliance from the first body-supporting element of the appliance when the actuatable member is then actuated from the second position to the first position.

2. The quick connect device of claim 1 further comprising two or more engagement members.

3. The quick connect device of claim 1 further comprising a cam member adapted to drive the one or more engagement members back and forth between their retracted and extended positions when the actuatable member is actuated back and forth between its first position and second positions.

4. The quick connect device of claim 3 wherein the actuatable member is adapted to drive the cam member back and forth between a lesser lift position and a greater lift position when the actuatable member is actuated back and forth between its first position and second positions.

5. The quick connect device of claim 4 wherein the actuatable member is actuated back and forth between its first position and second positions by rotating the actuatable member.

6. The quick connect device of claim 1 further comprising means to releasably lock the engagement members in an extended position.

7. The quick connect device of claim 1 wherein the quick connect device comprises a body having a tapered portion extending toward a side adapted to be oriented toward the knee of a user wearing the appliance.

8. An orthotic or prosthetic appliance with releasably connectable first body-supporting element and second element, comprising:

a quick connect device at least partially encapsulated within the first body-supporting element of the appliance, the first body-supporting element adapted to support and at least partially surround a portion of a wearer's body, for releasably connecting the first body-supporting element of the appliance to the second element of the appliance, the quick connect device including one or more engagement members that are drivable back and forth between a retracted position and an extended position by actuation of an actuatable member between a first position and a second position, the one or more engagement members being releasably engagable with the second element of the appliance to connect the second element of the appliance to the first body-supporting element of the appliance when the second element of the appliance is positioned adjacent and fit closely around that portion of the first body-supporting element where the quick connect device is at least partially encapsulated within the first body-supporting element and the actuatable member is actuated from the first position to the second position, the one or more engagement members being disengagable from the second element of the appliance to disconnect the second element of the appliance from the first body-supporting element of the appliance when the actuatable member is actuated from the second position to the first position.

9. The appliance of claim 8 wherein the appliance comprises a knee-ankle-foot orthosis.

10. The appliance of claim 8 wherein the first body-supporting element of the appliance is part of an ankle-foot orthosis.

11. The appliance of claim 8 wherein the appliance comprises a prosthetic device.

12. The appliance of claim 8 wherein the actuatable member is actuated back and forth between its first position and second positions by rotating the actuatable member.

13. The appliance of claim 8 wherein the quick connect device comprises a body having a tapered portion extending toward a side adapted to be oriented toward the knee of a user wearing the appliance.

14. A method of releasably connecting first body-supporting element and second element of an orthotic or prosthetic appliance, comprising:

at least partially encapsulating a quick connect device within the first body-supporting element of the appliance, the first body-supporting element adapted to support and at least partially surround a portion of a wearer's body, for releasably connecting the first body-supporting element of the appliance to the second element of the appliance, the quick connect device including one or more engagement members that are drivable back and forth between a retracted position and an extended position by actuation of an actuatable member between a first position and a second position, the one or more engagement members being releasably engagable with the second element of the appliance to connect the second element of the appliance to the first body-supporting element of the appliance when the second element of the appliance is positioned adjacent and fit closely around that portion of the first body-supporting element where the quick connect device is at least partially encapsulated within the first body-supporting element and the actuatable member is actuated from the first position to the second position, the one or more engagement members being disengagable from the second element of the appliance to disconnect the second element of the appliance from the first body-supporting element of the appliance when the actuatable member is actuated from the second position to the first position;

positioning the actuatable member such that the one or more engagement members are in a retracted position; and positioning the second element of the appliance adjacent and closely around that portion of the first body-supporting element where the quick connect device is at least partially encapsulated within the first body-supporting element and releasably connecting the first and second elements of the appliance by positioning the actuatable member such that the one or more engagement members are in the extended position and engaging the second element of the appliance.

15. The method of claim 14 further comprising the step of disconnecting the second element of the appliance from the first body-supporting element of the appliance by positioning the actuatable member such that the one or more engagement members are in a retracted position and disengaged from the second element of the appliance.

16. The method of claim 15 wherein the step of positioning the actuatable member such that the one or more engagement members are in a retracted position comprises rotating the actuatable member.

17. The method of claim 14 wherein the appliance comprises a knee-ankle-foot orthosis.

18. The method of claim 14 wherein the first body-supporting element of the appliance is part of an ankle-foot orthosis.

19. The method of claim 14 wherein the appliance comprises a prosthetic device.

20. The method of claim 14 wherein the step of positioning the actuatable member such that the one or more engagement members are in the extended position comprises rotating the actuatable member.

\* \* \* \* \*